United States Patent [19]

Neal

[11] 4,018,691
[45] Apr. 19, 1977

[54] ARYL SULFONATE-ALDEHYDE COMPOSITION AND PROCESS FOR ITS PREPARATION

[75] Inventor: John A. Neal, Bellingham, Wash.

[73] Assignee: Georgia-Pacific Corporation, Portland, Oreg.

[22] Filed: Aug. 28, 1975

[21] Appl. No.: 608,462

[52] U.S. Cl. .......................... 252/62.54; 252/62.52
[51] Int. Cl.² ..................... G01N 27/82; H01F 1/00
[58] Field of Search ......... 252/62.51, 62.52, 62.53, 252/62.54

[56] References Cited

UNITED STATES PATENTS

| | | | |
|---|---|---|---|
| 2,304,308 | 12/1942 | Hurd | 106/308 S |
| 2,694,656 | 11/1954 | Camras | 252/62.53 X |
| 3,344,063 | 9/1967 | Stratton | 252/8.5 |
| 3,546,107 | 12/1970 | Benko | 260/124 |
| 3,586,630 | 6/1971 | Ingersoll | 252/62.54 |
| 3,634,252 | 1/1972 | Graham | 252/62.54 |
| 3,635,819 | 1/1972 | Kaiser | 252/62.51 X |
| 3,843,540 | 10/1974 | Reimers et al. | 252/62.52 |

Primary Examiner—F.C. Edmundson
Attorney, Agent, or Firm—Peter P. Chevis

[57] ABSTRACT

A process for the preparation of aryl sulfonate-aldehyde condensate compositions having magnetic properties which may be water-soluble and compositions thereof are described.

18 Claims, No Drawings

ARYL SULFONATE-ALDEHYDE COMPOSITION AND PROCESS FOR ITS PREPARATION

The invention pertains to particular aryl sulfonate-aldehyde condensate compositions and a process for their preparation. More particularly it pertains to an iron composition of sulfonated phenol condensed with an aldehyde having ferromagnetic properties.

The technological advances made in the last few years have greatly increased the demand for magnetic materials. These advances have also created needs for magnetic material of unique properties. Ferromagnetism heretofore has been mainly associated only with the solid state where the existence of interatomic exchange forces is possible. Typical ferromagnetic solids such as metals, metal oxides, and alloys are by nature water-insoluble and considerable processing may be required to obtain such materials in the quasi-fluidic form which is necessary for certain applications, e.g., see U.S. Pat. Nos. 3,351,413; 3,620,584; and 3,635,819. A ferromagnetic composition which may be prepared in an aqueous medium would simplify the preparation of such ferromagnetic quasi-fluids and increase the scope of usage of such products. Recently as disclosed in Pat. application Ser. No. 439,579 filed Feb. 4, 1974 by co-workers William Scott Briggs et al, it was discovered that organically bound ferromagnetic composition may be prepared from sulfonated lignin and sulfonated tannin. It has not been unexpectedly discovered that ferromagnetic composition may also be obtained with particular aryl sulfonate-aldehyde polymers.

It is, therefore, an object of this invention to provide an aqueous composition having ferromagnetic properties. Another object is to provide a magnetic composition of aldehyde polymers of a sulfonated phenol. A further object is to provide a composition of sulfonated phenol condensed with formaldehyde having ferromagnetic properties. A still further object is to provide a process for the preparation of ferromagnetic composition in an aqueous medium.

The above and other objects may be attained according to a preferred embodiment of this invention by reacting an iron compound in the presence of particular aryl sulfonate-aldehyde polymers in an aqueous medium at a pH at least 5.5 in a manner which permits the formation of magnetite or other magnetic oxide of iron or other magnetic iron composition, e.g., by obtaining the iron by oxidation or otherwise, in the ferrous and ferric states under conditions for the formation of magnetite or other magnetic iron oxide or oxyhydroxide in an aqueous medium.

In carrying out the reaction to obtain the formation of magnetite or other magnetic iron oxides or oxyhydroxides in the presence of a sulfonated phenol condensed with an aldehyde, particular iron compositions are obtained associated with the organic moiety which are generally water-soluble and have a relative magnetic susceptibility or magnetization, on iron basis, in the range of magnetite. The magnetic composition; e.g., when dissolved in water, has the characteristics of a polyelectrolyte solution. No separation of the reacted iron from the organic moiety is obtained by filtration, high speed centrifugation, by passage through a gel permeation column, or by diffusion into agar gel indicating that the composition is not a dispersion or suspension of a magnetic iron oxide. While the present invention is not to be considered to be based on any particular theory of reaction mechanism, such reaction mechanism not being completely understood, it is believed that a composition is obtained where iron-oxygen polymeric units are bound in some manner to the organic moiety, presumably influenced to a certain extent by the sulfonate functional groups. Apparently, the reaction involves the initial formation of an iron hydroxide or oxyhydroxide possibly associated in some manner with organic sulfonate which is then converted to a magnetic composition by having the iron present in both ferrous and ferric states at the proper pH for formation of magnetite or other magnetic oxides or oxyhydroxides. After the initial formation of the iron hydroxide or oxyhydroxide ordinarily being obtained at a pH of 5.5 and above, additional alkali is consumed in the formation of the ferromagnetic product.

The term "ferromagnetic," as used herein, means being magnetic in a high degree like iron, cobalt, or nickel. Theoretically, magnetism of matter results from orientation and alignment of the magnetic moments of the electrons. Recently, classifications of magnetic behavior have been made in light of the atomic structure and the electronic or atomic interactions, instead of just the attractive force obtained upon subjecting the material to a magnetic field as done in the past. On this basis, a material such as magnetite, while highly magnetic, may be considered as "ferrimagnetic," since the material has electrons in more than one spin direction. Also, a ferromagnetic material may be reduced in particle size such that each of the particles is a single domain. In this state of subdivision, the ferromagnetic material is said to be "super paramagnetic" since the material displays combined properties of ferromagnetic and paramagnetic materials. For practical purposes and for uses for which the materials of this invention are to be used, the attractive force, as referred to herein as relative magnetic susceptibility, is the main magnetic property of importance. Thus, the term, ferromagnetic, is used herein to mean materials which are attracted to a magnet to a high degree, regardless of the interatomic relationships resulting in the magnetism or other properties which, at times, may be associated with ferromagnetism. The materials of the invention appear to have properties similar to those associated with ferromagnetic materials in fine particle size and are referred to as ferromagnetic when the material is attracted to a magnet with a significant force as compared to substantially pure iron, i.e., having a relative magnetic susceptibility, or a magnetization, of at least 60 percent of the relative magnetic susceptibility of substantially pure iron, based upon the iron content, when measured in a magnetic field of about 240 oersteds in the manner described in the examples below.

Processes previously used for the preparation of magnetic iron oxides or oxyhydroxides in an aqueous medium are contemplated as useful for the preparation of the magnetic composition as long as the conditions are not so drastic as to destroy the basic structure of the sulfonated phenol aldehyde polymer. Addition of the organic sulfonate to the aqueous medium prior to initiating the preparation of such products will result in the combination of the iron oxide with the alkyl aryl sulfonate in the formation of the product of the invention. A convenient method for carrying out the reaction is to dissolve the aryl sulfonate-aldehyde condensate and a water-soluble iron salt in water, and to react the mixture to convert it to the desired magnetic composition by adding alkali to the solution to an amount of about 1 equivalent per equivalent of iron. There will usually be a need for a change in the oxidation state of the iron in the presence of the alkali to obtain the iron in both the ferric and ferrous states in the desired proportions, e.g., approximately those present in magnetite. When a ferrous iron compound is used, the reaction of the iron with the lignosulfonate is usually carried out by heating the mixture with agitation in air to oxidize a portion of the iron. In addition to air, other oxidizing agents known to oxidize ferrous iron under alkaline conditions, such as for example hydrogen peroxide, a halogen as chlorine or bromine, and hypochlorite may be added under controlled conditions to provide the relatively mild oxidizing conditions sufficient to oxidize the ferrous iron without substantial oxidation or degradation of the sulfonate. When a mixture of ferrous and ferric iron compounds in the proper proportions to obtain magnetite are added to the heated solution at a suitable pH, the oxidation is not necessary and the ferromagnetic composition may be obtained upon heating the mixture with sufficient alkali to form the ferromagnetic composition.

A ferric iron compound may also be used as the sole iron compound. When this is done, the reaction is carried out under reducing conditions to reduce a portion of the ferric iron to the ferrous state or to reduce all of the ferric iron substantially to the ferrous state and then carrying out the reaction the same as noted above.

Various methods for condensation of phenol with aldehydes may be used for the condensation of the sulfonated phenol with the aldehyde for use in preparation of the magnetic composition. Generally, the impurities which may be present in the product manufactured by most of the processes do not or are not present at levels which are detrimental. A convenient method for the preparation of the aryl sulfonate is to sulfonate the particular phenol with sulfuric acid and then react the sulfonated phenol with the aldehyde similar to that described in U.S. Pat. Nos. 2,681,312 and 3,214,373. Preferably the sulfonation of the phenol is carried out such that predominantly a mono-sulfonated phenol is obtained. Products having a wide range of sulfonate sulfur content may be used for the preparation of the compositions. The amount of iron which can be associated with the sulfonated phenol condensed with the aldehyde appears to increase with increase in sulfonate sulfur content. However, total sulfonation of the phenol is not desirable since sufficient reactive sites or positions should remain on the phenol molecule for polymerization or condensation with the aldehyde. Generally, the polymerization with the aldehyde is carried out, without insolubilization of a large portion of the condensate, until sufficiently large molecules are obtained to maintain appreciable amounts of the magnetic iron compound associated with it in solution. Apparently the larger molecules of the condensate have a greater capacity to maintain large amounts of iron in magnetite form in soluble state. Thus, a higher degree of polymerization is advantageous in this respect. The extent of polymerization obtained with the aldehyde may also be controlled by limiting the amount of aldehyde condensed with the sulfonated phenol. The amount of aldehyde reacted with the sulfonated phenol may be varied but is generally in the range of from about ⅓ to ½ moles of aldehyde per mole of phenol. In the formation of the magnetic composition by reaction of the iron compound with the aldehyde condensed sulfonated phenol, some cross-linking may also be obtained resulting in a further increase in the molecular weight of the molecule. Thus, generally it is desirable not to condense the sulfonated phenol with the aldehyde to the extent that the additional cross-linking obtained by the reaction of the condensate with the iron would result in insolubilization of a large portion of the magnetic composition, unless water solubility of the magnetic composition is not necessary for the ultimate use of the product.

In addition to the polymerization of the sulfonated phenol with the aldehyde, the condensate upon condensation may be oxidized prior to being reacted with the iron compound in the formation of the magnetic composition. Upon oxidation of the condensed sulfonated phenol and aldehyde, the amount of iron which may be associated with the condensate increases indicating that possibly some association of the magnetic iron composition to the organic moiety may also be effected through the carboxylic groups which are formed as well as the sulfonate groups. Oxidizing agents such as disclosed in U.S. Pat. No. 3,214,373 which include hydrogen peroxide, ozone, lead dioxide, chromic acid, chlorine, alkali and alkaline earth metal hypochlorites, alkali metal chromates, alkali metal permanganate, alkali metal persulfate, alkali metal perborate, and combinations thereof. Oxidation with chromate or dichromate may result in some cross-linking and would not be used if the further increase in molecular weight of the condensate is not desired.

The aldehyde reacted with the sulfonated phenol is preferably formaldehyde, but other aldehydes having up to 6 carbon atoms, such as formaldehyde, acetaldehyde, and heterocyclic aldehydes, such as furfural and hydroxymethylfurfural and aromatic aldehydes such as benzaldehyde may be employed. Dialdehydes may also be used but the reaction conditions have to be controlled more carefully to keep the product from condensing to the point of insolubility. The aldehydes which are free of alpha hydrogen are preferred. In addition to phenol itself, other phenols having not more than one additional substitution on the aromatic ring such as cresol and guaiacol may be used. Also, in addition to the monohydric phenols, dihydric phenols are operative but due to their reactivity the reaction may be more difficult to control.

In the reaction with the iron compound, the concentration of the aryl sulfonate-aldehyde condensate in the solution may be widely varied from less than 1% to over 30 percent with a practical concentration for many of the sulfonate condensates being in the range of ½ to 20 weight percent. Concentrations in the range of 3 to 10 percent are often used. Any concentration may be used except that at higher concentrations the viscosity of the reaction mixture may be sufficiently increased to make it more difficult to handle and react.

The amount of iron added to the aqueous medium with the sulfonated phenol condensate is generally in excess of a stoichiometric amount of iron, expressed as ferric iron, necessary for reaction with the sulfonate and carboxyl groups in the condensate. Since the magnetic properties of the composition depend upon the iron content, compositions having larger amounts of iron are preferred. Generally the iron compound is added in a sufficient amount to obtain products having about 10 percent of iron, preferably from 16 to 25 weight percent of iron. The amount of iron which can be combined with a particular sulfonated phenol condensate reaches a limit beyond which no additional iron becomes associated with the organic moiety regardless of the excess of iron added. Compositions containing iron from about 12 to 16 percent and above are preferred. In reactions with relatively concentrated solutions or with relatively high concentrations of iron in which high viscosities may be obtained, the reaction may be carried out with the iron and alkali being added continuously or in more than one step to minimize the viscosity effect. For example, a sufficient amount of an iron salt may be added to a sulfonated phenol condensate solution to provide a product containing 10 percent or so of iron. After the addition of the iron salt to the solution, the alkali would be added to the solution to increase the pH to the desired level and then the product heated until substantially all of the iron is converted to a magnetic form. Additional amounts of the iron salt may be added to this mixture and the process repeated. By this procedure, products containing 20 percent and higher of iron may be prepared, especially with the sulfonated phenol-aldehyde condensates which have been oxidized after condensation of the sulfonated phenol with the aldehyde.

Any iron compound which is soluble in water under acidic conditions and forms iron hydroxide upon addition of alkali may be used in the reaction with the organic sulfonates to form the ferromagnetic composition. Inorganic salts, such as chlorides, bromides, nitrates, and sulfates are preferred. However, organic iron compounds such as the formates or acetates may also be used. These compounds may be dissolved in water prior to addition to the condensate solution or may be added directly to the solution. The method of adding the iron compound to the condensate solution is immaterial as long as the iron is in the condensate solution at the time the desired pH is obtained to form iron hydroxide or iron oxyhydroxide. This can be generally accomplished by intermixing the iron compound with the sulfonated phenol condensate solution before the addition of the alkali or the alkali can be added to the solution prior to the addition of the iron compound. In these situations, the proper pH conditions are obtained to effect the iron hydroxide or iron oxyhydroxide formulation. The same result is obtained when the iron compound in the dry state is added to the condensate solution. It is not necessary to use an iron compound which is completely soluble in water or in the solution. However, the compound must be at least partially soluble to supply sufficient iron ions to initiate the reaction which would then permit additional iron to dissolve and react.

The ratio of alkali, based upon the amount of iron added, utilized in the formation of the magnetic composition is generally in a small excess of the amount necessary for the formulation of magnetite or other magnetic oxides. Although products with significant magnetic susceptibility and yield may be obtained by reacting ⅛ equivalent or less of alkali per equivalent of iron, about 1 equivalent of alkali per equivalent of iron is preferred. Generally, an amount in the range of about 0.9 to 1.5 equivalents of alkali per equivalent of iron is used, and usually from 1.1 to 1.25 equivalents. With a small excess over one equivalent, a sufficient amount of alkali is present, if necessary, to neutralize or bring the reaction mixture to a desired pH and still have about one equivalent of alkali available for reaction. No particular advantage is gained in using a large excess of alkali. Normally, upon addition of the alkali, the alkali will begin to be consumed immediately upon addition. As the reaction proceeds, the pH continues to decrease. The amount of alkali consumed in the reaction does not vary greatly whether the alkali is added all at once or added continuously to provide the necessary presence of alkali and maintain the reaction mixture at the desired pH of at least about 5.5. However, when the reaction is carried out at a constant pH, it is generally carried out at a pH of at least 6, preferably at a pH in the range of 7 to 10.

Any alkali which will provide hydroxide groups without insolubilizing the sulfonated phenol-aldehyde condensate may be used in the reaction with the iron and condensate or with the hydroxides and oxides of alkali metals, such as sodium, potassium, and lithium being preferred. Sodium hydroxide is most often employed due to cost and availability. Ammonium hydroxide and organic hydroxides, such as tetramethylammonium hydroxide, may also be used. In addition, alkaline earth metal hydroxides and oxides, such as calcium and magnesium hydroxide, may also be used.

The temperature at which the iron compound and condensate solution are mixed and at which the pH adjustment is made is immaterial and may be widely varied from below room temperature to the temperature used for reacting the mixture in formation of the magnetic composition. However, when using the preferred embodiment of the invention, the condensate solution and iron mixture is preferably heated with the alkali at a temperature of at least 40° C and, generally, a temperature of at least 80° C is used to obtain a more rapid reaction rate. At lower temperatures, the rate of reactions or the formation of the ferromagnetic iron product is relatively slow which requires controlling the rate of oxidation or reduction of the iron in the mixture to correspond to this rate to have the change in oxidation state of the iron extend over most of the reaction period. A reaction temperature in the range of 90° C to 140° C is preferred. At the preferred temperatures, a reaction time in the range of from 15 minutes to 4 hours may be generally sufficient to substantially convert all of the iron to the magnetic form for the mixture concentrations normally used. For the more concentrated, highly viscous solutions or reaction mixtures, longer times may be required which may be extended, or example, to 24 or more hours at these temperatures without deleterious effect. While a higher temperature may have no particular disadvantages, the reaction may be most conveniently carried out in about 1 to 4 hours at temperatures of from 99° C to 100° C without the use of pressure equipment. At these temperatures, the rate of reaction is sufficiently rapid to correspond favorably to the rate of oxidation which can be obtained from ferrous to ferric iron by relatively mild agitation of the reaction mixture in air. However, temperatures from room temperature or below up to the thermal decomposition of the organic sulfonates may be used. The rate of reaction increases with temperature so that with reaction temperatures of 200° C and above, just heating of the mixture to that temperature may be sufficient to substantially complete the reaction, while at 25° to 40° C from 12 to 48 hours may be required.

After completion of the reaction, the reaction mixture is cooled and may be processed further by known methods to separate the magnetic composition from the inorganic salts or other impurities which may be present. The reaction mixture may contain soluble inorganic salts, such as salts of the cations of the alkali and anions of the iron compound, which have a diluent effect. These salts and other low molecular constituents may be conveniently removed by use of dialysis or other physical separation methods such as gel permeation. The solution containing the magnetic composition may also be evaporated and dried, using accepted methods. Once the composition has been formed, it is stable in presence of alkali and acids from pH 1 to 13 without decomposition. The composition obtained is ferromagnetic in solution as well as when dried. The composition may be dried and redissolved in water numerous times without significantly affecting the magnetic susceptibility or the stability of the composition or aqueous medium.

The ferromagnetic iron composition may be used in the dry form or in an aqueous medium. In the dried form, the product may be pressed with a binder to form magnetic bodies of different shapes and used to replace iron oxide and other magnetic materials in certain applications. The product may also be used in magnetic weaving, magneto location, and for other purposes where the water-solubility of the composition is desirable. The water-solubility or dispersibility of the composition also greatly simplifies its use in material separation processes, such as in ore flotations, where separations are enhanced by magnetically-induced variations of apparent fluid density. The composition also may be used in phase separations such as those of liquid extraction processes where the partitioning of the phase may be magnetically improved.

In addition to using iron only, other polyvalent metals such as nickel, manganese, and other metals known to form ferrites or magnetic oxy or hydroxy compounds with iron may be used in combination with the iron. The metal compound with the iron compound may be added to the organic sulfonated phenol-aldehyde condensate solution in proper proportions for the formation of the ferrite or desired composition and reacted in a manner similar to that when iron is used alone, with some adjustments being made to obtain the optimum formation of the respective metal oxide for the formation of the ferrite or magnetic composition.

The following examples further illustrate the invention.

EXAMPLE I

A ferromagnetic composition was prepared from a condensation product of sulfonated phenol and formaldehyde.

The sulfonated phenol-aldehyde condensation product was prepared by dissolving 75 grams of phenol in 131 grams of concentrated sulfuric acid and heating the mixture for 30 minutes at 100° C. The reaction product was cooled to 60° C and then a solution of 78 grams of 40% formaldehyde in 232 grams of water was added and the mixture was heated for about 40 minutes at 85° C. The reaction mixture was cooled by adding 360 milliliters of water, neutralized to pH 6 by adding a lime slurry and then to pH 9.8 by adding sodium hydroxide. The reaction mixture was then used in preparation of the ferromagnetic composition.

A portion of the above reaction mixture containing 10 grams of solids was diluted to 300 milliliters and heated to 90° C. To the solution of the sulfonated phenol-formaldehyde polymer one gram of ferric iron, as ferric sulfate hydrate, and one gram of ferrous iron, as ferrous sulfate hydrate were dissolved. Sodium hydroxide in an amount of 3.47 grams was added as a 50% solution. The solution was stirred and heated at 90° to 95° C for 2½ hours while air, free of carbon dioxide, was bubbled through the mixture. The mixture was cooled to room temperature and centrifuged for 1 hour at 8,000 × gravity. The soluble portion contained 1.4 grams of iron and was dialyzed to remove the inorganic impurities. After purification, the product had an iron content of 16.9% on a solid basis and a relative magnetic susceptibility of 6.5 grams per gram of iron.

The relative magnetic susceptibility of the product was measured using a procedure similar to that described by D. F. Evans in the Journal of the Chemical Society (A), London, (1967), 1670. In the procedure, two similar magnets were fixed in position on the pan of an analytical balance with the north pole of one of the magnets facing the south pole of the other. The pole faces of each of the magnets were square having a dimension of 2.5 cm on edge. The magnets were placed with a pole gap of 3.3 cm at the bottom and 3.5 cm at the top. In the sample area the magnetic field generated by the magnets was about 240 oersteds. In determining the magnetic susceptibility or the attractive force of the magnetic field on the product, the sample was ground into a fine uniform powder and packed into a Pyrex test tube of the type normally used for nuclear magnetic resonance measurements. The test tube had an inside diameter of 4.5 millimeters. The sample tube was rigidly fixed between and near the top of the two magnets. The relative magnetic susceptibility or the attractive force was obtained by noting the change in weight of the magnets in the presence of the sample. Samples of about 15 milligrams were tested which when packed in the test tube filled the tube to a height of about 2 to 3 millimeters. The relative magnetic susceptibility was determined by dividing the change in weight of the magnets obtained in grams by the amount of iron in the sample in grams. The relative magnetic susceptibilities or the attractive forces of three samples of magnetite or $Fe_3O_4$ of laboratory grade obtained from three sources measured under the above procedure were in the range of 3.3 to 3.6 grams per gram of iron. For substantially pure iron of standard of reference grade, the attractive force or the relative magnetic susceptibility was 2 grams per gram of iron.

To illustrate that the ferromagnetic composition obtained was not a suspension of magnetite, an aqueous solution of the ferromagnetic product prepared above was passed through a chromatographic column packed with Bio-Gel A-5m Agarose beads in water. The column packing was designed for gel filtration in an operating molecular weight range of 10,000 to 5,000,000. No separation was visibly observed as the material was eluted from the column with water. The effluent was collected in 3 fractions and analyzed for organic sulfur, iron content, and the relative magnetic susceptibility. The results and the weight distribution obtained of the three samples are shown in the following table:

| Fractions | Solids, Grams | Organic Sulfur Wt, % of Solids | Iron Content % of Solids | Magnetic Susceptibility g/g Fe |
| --- | --- | --- | --- | --- |
| 1 | 0.25 | 5.0 | 21.3 | 6.2 |
| 2 | 0.30 | 4.8 | 23.8 | 6.3 |
| 3 | 0.20 | 6.0 | 15.8 | 6.0 |

EXAMPLE II

A ferromagnetic composition was prepared from a sulfonated phenol-formaldehyde condensation product which was oxidized prior to preparation of the magnetic composition.

A sulfonated phenol-formaldehyde condensation product was prepared in a manner similar to that described above. To about 125 grams of the neutralized reaction solution of the sulfonated phenol-formaldehyde polymer containing about 25 grams of solids, 8.3 grams of 30% hydrogen peroxide were added. The mixture was mixed and allowed to stand at room temperature for 24 hours.

A portion of the reaction solution of the oxidized polymer above containing about 10 grams of polymer solids was diluted to 300 milliliters by addition of water and heated to 90° C. Ferric sulfate hydrate, ferrous sulfate hydrate and sodium hydroxide were added as in Example I and the mixture heated at 90° to 95° c for 2½ hours while being stirred and air, free of carbon dioxide, being bubbled through the mixture. After cooling to room temperature, the soluble portion was purified by dialysis and found to contain 19.5 weight percent iron on a dry basis. This represented about 95% of the total iron added. The relative magnetic susceptibility of the product measured in the manner described in Example I was 4.1 grams per gram of iron.

What is claimed is:

1. A ferromagnetic, iron reacted sulfonated phenol-aldehyde condensation product.

2. A condensation product of a sulfonated phenol and aldehyde chemically combined with iron to form a ferromagnetic iron composition.

3. A composition of claim 2 wherein the sulfonated phenol-aldehyde condensation product is chemically combined with iron to form a magnetic iron composition by the formation of magnetic iron oxide or oxyhydroxide in an aqueous solution of a sulfonated phenol condensed with an aldehyde.

4. A composition according to claim 3 wherein an iron compound is dissolved in the aqueous solution of the sulfonated phenol-aldehyde condensation product and converted to magnetic iron form.

5. A composition according to claim 4 wherein the sulfonated phenol-aldehyde condensation product is sulfonated phenol condensed with formaldehyde.

6. A composition of claim 4 wherein an iron compound and a sulfonated phenol-aldehyde condensation product are dissolved in an aqueous medium and mixed in the presence of an alkali at a temperature up to 230° C at a pH of at least about 5.5 to form a magnetic composition, said iron compound being dissolved in an amount of at least twice the stoichiometric amount, as ferric iron, to react with the sulfonate groups of the condensation product, said mixture being mixed under conditions to obtain the iron in the ferrous and ferric states.

7. A composition according to claim 6 wherein the iron compound and sulfonated phenol-aldehyde condensation product are mixed at a pH of at least 6 until from 0.9 to 1.5 equivalents of alkali per equivalent of iron are reacted and the concentration of the sulfonated phenol-aldehyde condensation product in the solution is from 0.5 to 20 weight percent.

8. A composition according to claim 7 wherein the iron compound is a water-soluble inorganic iron salt and the condensation product is a mono-sulfonated phenol condensed with formaldehyde.

9. A composition according to claim 8 wherein the iron salt is dissolved in the solution in an amount to supply from 10 to 40 weight percent iron, based upon the condensation product and the mixture heated until about 1 equivalent of the alkali per equivalent of iron is reacted with the iron salt and condensation product.

10. A composition according to claim 9 wherein the mixture is heated at a temperature in the range of 90° to 140° C at a pH in the range of 7 to 10 in the presence of sodium hydroxide, and the iron salt is a ferrous salt.

11. A composition according to claim 10 wherein the water-soluble ferrous salt is a ferrous sulfate added in an amount to supply from 20 to 40 weight percent iron based on solids and the mixture is heated at a temperature in the range of 90° to 100° C with agitation in air to oxidize part of the iron from ferrous to ferric states.

12. A composition according to claim 10 wherein a compound of a metal selected from the group of nickel, manganese and mixtures thereof is added with the ferrous salt.

13. A composition according to claim 10 wherein said ferrous salt is added as a mixture of ferrous and ferric salts.

14. A composition of claim 13 wherein said ferric and ferrous compounds are present in proportion suitable for the formation of a magnetic iron oxide.

15. A process for the preparation of a magnetic composition, which comprises dissolving a water-soluble iron salt and a condensation product of a sulfonated phenol with an aldehyde in water in an amount to obtain up to 30 weight percent of the condensation product and at least 9 weight percent iron, based upon the weight of the product, adding from 0.9 to 1.5 equivalents of an alkali metal hydroxide per equivalent of iron to the solution, and heating the mixture at a temperature in the range of 40° to 230° C for from 0.5 to 24 hours to react the iron with the material to form a magnetic composition, said mixture being heated with the iron being in ferrous and ferric states.

16. A process according to claim 15 wherein the water-soluble iron salt is an inorganic salt and is added in an amount of from 20 to 50 weight percent, and the condensation product is at a concentration of from 3 to 10 weight percent in the solution.

17. A process according to claim 16 wherein the condensation product is sulfonated phenol condensed with formaldehyde and the mixture is heated in the presence of sodium hydroxide at a temperature in the range of 90° to 140° C for from 0.25 to 4 hours.

18. A process according to claim 17 wherein the iron salt is ferrous sulfate and the mixture is heated in presence of air to oxidize a portion of the iron from ferrous to ferric state.

* * * * *